United States Patent [19]

Pitsillides et al.

[11] Patent Number: 5,544,656

[45] Date of Patent: Aug. 13, 1996

[54] METHOD AND APPARATUS FOR MYOCARDIAL WALL MEASUREMENT

[75] Inventors: Koullis F. Pitsillides, Sacramento; John C. Longhurst, Winters, both of Calif.

[73] Assignee: The Regents of the University of California, Oakland, Calif.

[21] Appl. No.: 349,356

[22] Filed: Dec. 2, 1994

[51] Int. Cl.⁶ .................................................. A61B 8/00
[52] U.S. Cl. ............................. 128/661.04; 128/662.03
[58] Field of Search ........................ 128/660.01, 660.02, 128/661.04, 661.07, 661.1, 662.03, 662.04

[56] References Cited

U.S. PATENT DOCUMENTS

| | | | |
|---|---|---|---|
| 4,947,854 | 8/1990 | Rabinovitz et al. | 128/662.060 |
| 4,966,150 | 10/1990 | Etienne et al. | 128/661.040 |
| 4,993,427 | 2/1991 | Barr et al. | 128/661.070 |
| 5,243,987 | 9/1993 | Shiba | 128/661.070 X |
| 5,289,820 | 3/1994 | Beach et al. | 128/661.070 |
| 5,360,006 | 11/1994 | Geiser et al. | 128/653.1 |

OTHER PUBLICATIONS

Donnerstein, R. et al., "Digital Range–Gated Echocardiographic Tracking", Med. Iustr. vol. 12#3 May–Jun. 1978.

Pitsillides et al., Biotelemetry of Cardiovascular Measurements in Miniswine, IEEE Transactions on Biomedical Engineering, pp. 982–986, Sep. 1992.

Wildi et al., Dynamics and Limitations of Blood/Muscle Interface Detection Using Doppler Power Returns, IEEE Transactions on Biomedical Engineering, pp. 565–573, Oct. 1980.

Hartley et al., Doppler Measurement of Myocardial Thickening with a Single Epicardial Transducer, AM J Physiol 245, pp. H1066–H1072, 1983.

Hartley et al., Range Gate Tracking for Doppler Measurement of Myocardial Thickening, Ultr. Med. Biol. Abstract, Suppl. 1, p. 560, 1985.

Pitsillides et al., Multi–Channel Biotelemetry of Myocardial Hemodynamic Variables in Miniswine, Federation of American Societies of Experimental Biology, Washington DC, 1990.

*Primary Examiner*—Francis Jaworski
*Attorney, Agent, or Firm*—John P. O'Banion

[57] ABSTRACT

A closed-loop single-crystal ultrasonic sonomicrometer capable of identifying the myocardial muscle/blood interface and continuously tracking this interface throughout the cardiac cycle using a unique piezoelectric transducer. During steady-state, a reference volume $SV_m$ is adjusted so that it remains within the myocardium while half of an interface volume $SV_i$ is in the myocardium and one-half is in the ventricular chamber. Every 100 ns, a 0.5 µs duration ultrasonic burst of 10 MHz pulses is transmitted from the piezoelectric transducer. Myocardial layers and red blood cells in the ventricular chamber reflect the ultrasonic energy back to the piezoelectric transducer. The echoes are then amplified and applied to a Doppler decoder, which then mixes them with a local oscillator signal having a 2 kHz offset relative to the transmitted signal. When the offset signal is mixed with returning ultrasonic echoes, the resulting Doppler signals are shifted in the frequency domain by 2 kHz. The received Doppler signal is then processed by an amplitude-locked-loop circuit which maintains the steady state throughout the cardiac cycle. Initially, the Doppler decoded signal is sampled at two distinct time intervals corresponding to sample volumes $SV_m$ and $SV_i$. The outputs from these two sample volumes are then bandpass filtered to remove frequencies contributed by red blood cells. The true RMS values from both sample volumes are then compared and an error signal is generated. The integrated error signal is adjusted for correct depth placement and applied to a voltage-controlled delay circuit. The amplitude-locked-loop circuit continuously adjusts the position of the two sampled volumes $SV_m$ and $SV_i$, so that they always remain within, and thereby effectively track, the muscle/blood interface. As a result, the apparatus can measure absolute myocardial wall thickness.

16 Claims, 12 Drawing Sheets

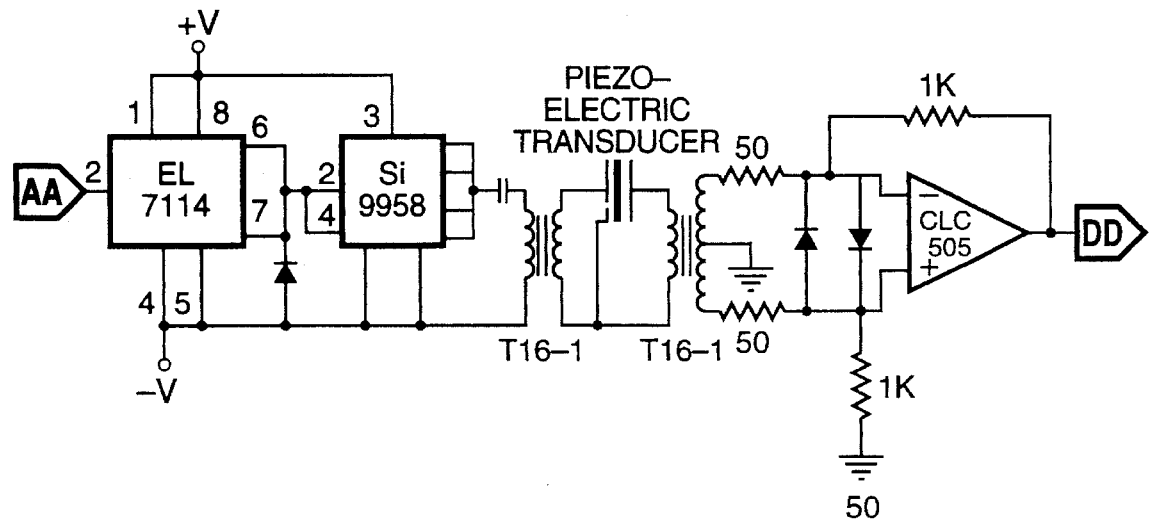
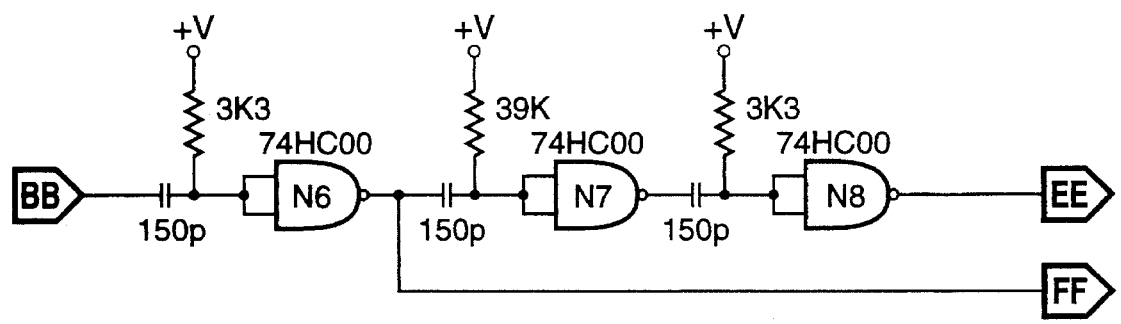
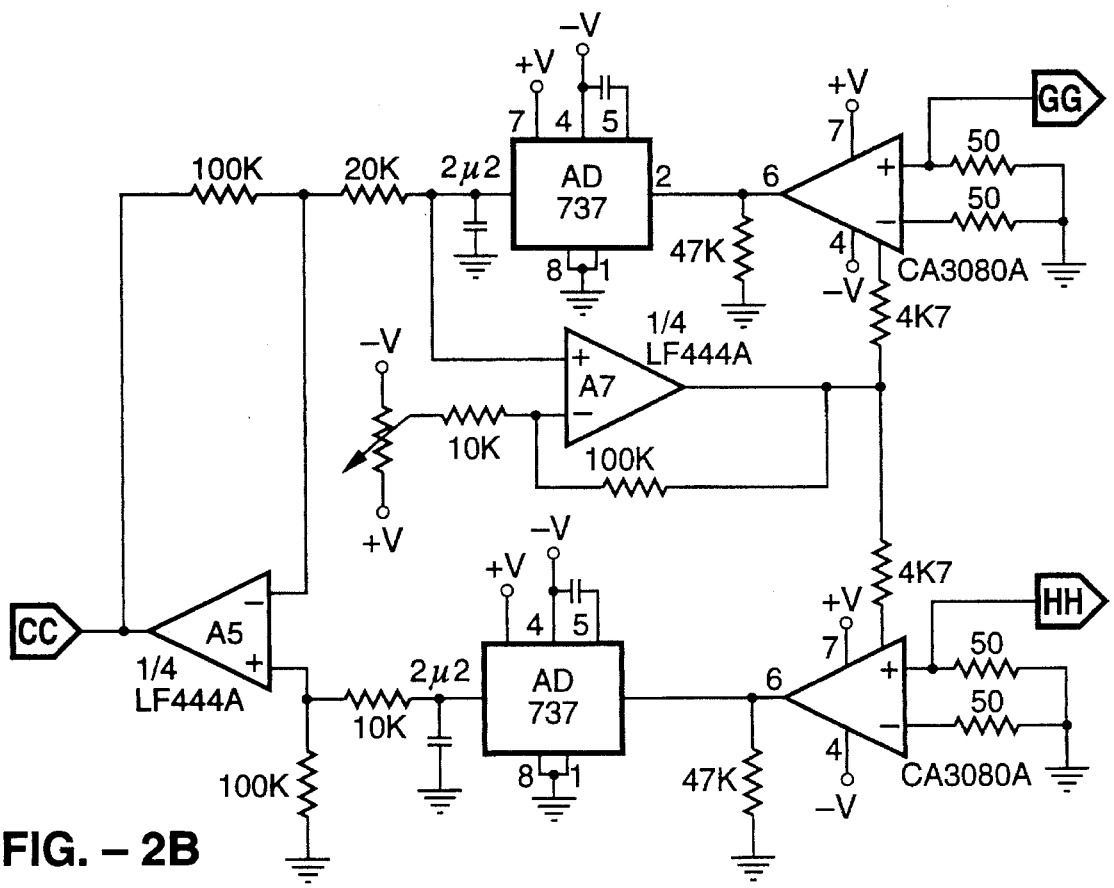
FIG. – 2B

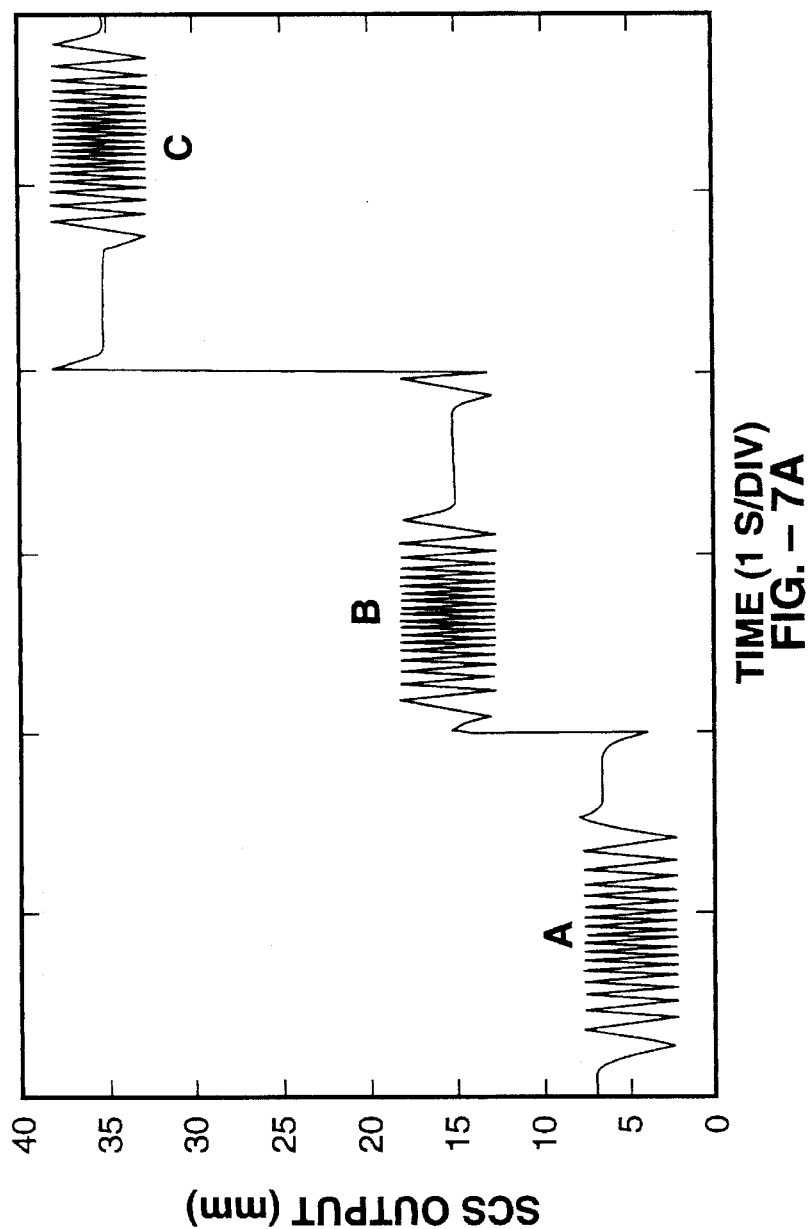

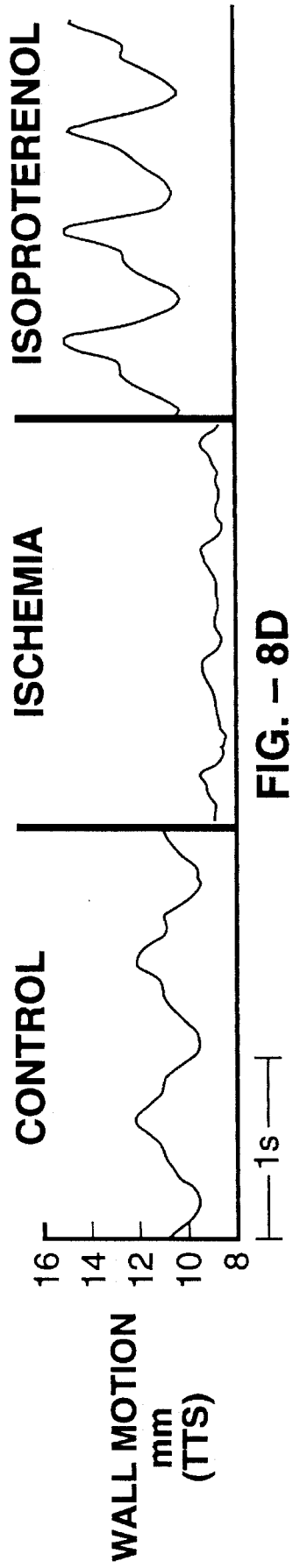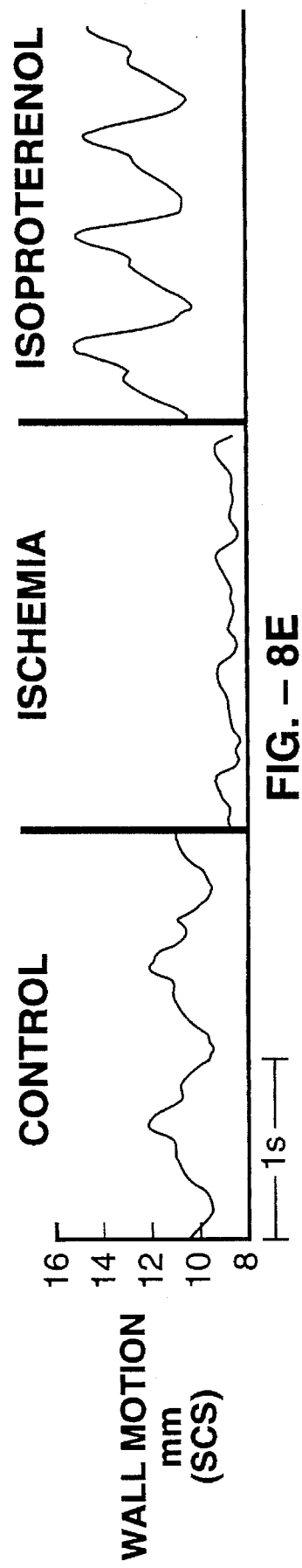

METHOD AND APPARATUS FOR MYOCARDIAL WALL MEASUREMENT

BACKGROUND OF THE INVENTION

1. Field of the Invention

The present invention pertains generally to measuring the thickness of the myocardial wall in a heart, and more particularly to a single-crystal ultrasonic sonomicrometer for measurement of absolute myocardial wall thickness.

2. Description of the Background Art

Measurement of myocardial wall thickness, as well as end-systolic and end-diastolic dimensions, are important in evaluating the effects of changes in regional myocardial function and contractility, including evaluating myocardial oxygen supply and demand, in acute and chronic animal studies. Presently, two types of commercially available instruments exist that utilize ultrasound to measure myocardial wall thickness in real-time. These include the transit-time sonomicrometry system and more recently, the Doppler echo displacement system.

A transit-time sonomicrometer uses two crystals, one as a transmitter and the other as a receiver, and operates by measuring the time required for ultrasound to travel between the transmitting and receiving transducers. An advantage of this system is its ability to provide an absolute dimension signal output calibrated in units of distance. However, the system has several disadvantages such as (1) it is necessary to insert a transducer through the myocardium, which can damage the myocardial nerve and blood vessel supply of the myocardial wall, (2) it is difficult to position precisely the endocardial crystal at the tissue/blood subendocardial interface, and (3) it can be difficult to maintain good alignment at all times throughout the cardiac cycle for short term and particularly during longer duration studies (>12 weeks).

The Doppler echo displacement system addresses the necessity to avoid damage to the myocardium by using a single epicardial ultrasonic transducer. A non-tracking system was developed initially, while a tracking system has been developed more recently. The operating principles for both instruments are similar and are analogous to the operating principles of a blood-flow velocity meter.

In a non-tracking Doppler echo displacement system, a short burst of ultrasound pulses is transmitted from a single transducer sutured to the epicardium. After the transmission burst ends, the receiver circuits are enabled and the system receives echoes returning from underlying myocardial layers, using the same transducer. Phase detectors then measure the quadrature phase of the returned echoes that pass through a static sample volume. Integrating the phase zero crossings throughout the cardiac cycle provides a measurement of the velocity of myocardial layers passing through the sample volume. In theory, assuming that the velocity of the endocardium is changing linearly with respect to the velocity of the epicardium, a good estimate of myocardial thickening is expected. However, to avoid interference from ventricular chamber blood flow, the depth to which the sample volume can be advanced is limited to 1–2 mm less than the minimum end-diastolic excursion. An advantage of this system is the absence of damage to myocardium by the single epicardial transducer; however, the disadvantages are: (1) the instrument provides only an estimate of displacement rather than a measurement of absolute myocardial wall thickness, (2) its sample volume must be placed in a fixed location 1–2 mm less than the minimum end-diastolic excursion, a requirement that does not allow measurement of function from the entire subendocardium, the area most vulnerable to ischemia, and (3) an external reset mechanism (e.g. ECG) must be used to avoid baseline wandering, a requirement that imposes a preselected minimum end-diastolic dimension, a value that normally varies during the course of an experiment.

The tracking Doppler echo displacement system was subsequently developed to address deficiencies of the non-tracking version. The system function is nearly identical to that of the non-tracking system with the exception of a feedback circuit that is used to adjust the position of the sample volume. However, the tracking system does not employ a method to ensure that it reliably tracks the endocardial wall; rather, during the cardiac cycle, the feedback circuit adjusts the sample volume position in response to the integrated velocity profile of echoes passing through the sample volume. Like the non-tracking system, the tracking Doppler displacement system uses a synchronization signal, such as the R-wave of an ECG, to reset the tracking gate back to a predetermined end-diastolic position, set at the beginning of the experiment. The echoes reflected back to the epicardial transducer, and detected in the sample volume, usually are not from a single myocardial layer but rather from multiple reflectors. Since there is only one reference point throughout the R-wave synchronized cardiac cycle, however, it is possible to lose track of echoes reflected from the myocardial layer selected during R-wave synchronization, and follow a different myocardial layer. The system is designed to track all echoes that pass through the sample volume at the time of the synchronization pulse. This feature results in an end-diastolic dimension that does not change from beat-to-beat unless the user repositions the depth of the sample volume and recalibrates. The synchronization pulse resets the sample volume to the pre-selected position, regardless of its true position, which may have changed during an intervention. This system requires the user to frequently reposition the end-diastolic range of the instrument and to recalibrate for proper operation. Advantages of the tracking Doppler echo displacement system are: (1) the system only requires one transducer, placed on the epicardial surface, and (2) the output signal can be calibrated in absolute units of distance. However, its disadvantages are: (1) the system does not track the endocardial surface, so the measurement of myocardial wall thickness dimension may not represent actual wall excursion, and (2) the system is unable to continuously measure real-time changes in end-diastolic dimensions throughout interventions, without readjustment and recalibration.

Therefore, there is a need for an apparatus which can measure myocardial wall thickness in absolute units of distance between the entire epicardium and endocardium throughout the cardiac cycle using a single epicardial transducer, which operates without requiring frequent recalibration or other adjustments, and which is easy to use and calibrate. The present invention satisfies those needs, as well as others, and overcomes the deficiencies in the myocardial wall thickness measurement instruments heretofore developed.

SUMMARY OF THE INVENTION

By way of example, and not of limitation, the present invention generally comprises a closed-loop single-crystal ultrasonic sonomicrometer capable of identifying the myocardial muscle/blood interface and continuously tracking this interface throughout the cardiac cycle using a unique piezoelectric transducer. During steady-state, a reference volume $SV_m$ is adjusted so that it remains within the myocardium while half of an interface volume $SV_i$ is in the ventricular chamber. Every 100 ns, a 0.5 μs duration ultrasonic burst of 10 MHz pulses is transmitted from the piezoelectric transducer. Myocardial layers and red blood cells in the ventricular chamber reflect the ultrasonic energy back to the piezoelectric transducer. The echoes are then amplified and applied to a Doppler decoder, which then mixes them with a local oscillator signal having a 2 kHz offset relative to the transmitted signal. When the offset signal is mixed with returning ultrasonic echoes, the received Doppler signal is shifted in the frequency domain by 2 kHz. The signal is then processed by an amplitude-locked-loop (ALL) circuit which maintains the steady state throughout the cardiac cycle. Initially, the received signal is sampled at two distinct time intervals corresponding to sample volumes $SV_m$ (reference) and $SV_i$ (interface), where the reference volume is positioned in the muscle, while one-half of the interface volume is positioned in the muscle and one-half is positioned in the blood. The outputs from these two sample volumes are then bandpass filtered to remove frequencies contributed by red blood cells. The true RMS values from both sample volumes then are compared and an error signal is generated. The integrated error signal is adjusted for correct depth placement and applied to a voltage controlled delay circuit. Thereafter, the ALL circuit continuously adjusts the position of the two sample volumes $SV_m$ and $SV_i$, so that they always remain within, and thereby effectively track, the muscle/blood interface. This process allows the apparatus to measure absolute myocardial wall thickness.

By locating the range-gated sample volumes in the myocardial muscle, the present invention has a much greater signal to noise ratio than systems which locate their sample volumes in the blood. Additionally, by employing a specially designed ultrasonic transducer, the operation during both the transmitting and receiving phases is optimized. Further, by using only one transducer, potential damage to the myocardium from insertion of an endocardial transducer used in two-crystal sonomicrometer systems is eliminated. In addition, unlike Doppler echo displacement method systems that can only estimate myocardial thickening, the present invention is capable of measuring the actual dimension of the endocardial wall throughout the cardiac cycle.

An object of the invention is to provide an apparatus which uses a single piezoelectric transducer placed on the epicardium which results in minimal or no injury to the muscle.

Another object of the invention is to eliminate the need for insertion of an endocardial transducer that may potentially cause damage to the myocardium.

Another object of the invention is to measure the actual dimension of the endocardial wall throughout the cardiac cycle.

Another object of the invention is to track the endocardial interface to provide a measurement of myocardial wall function that can be calibrated in absolute units of distance.

Another object of the invention is to provide an apparatus which is easy to use and which requires only one adjustment and a calibration at the beginning of the experiment.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 2A through FIG. 2C is a schematic diagram of a single-crystal ultrasonic sonomicrometer shown in FIG. 1.

FIG. 7A and FIG. 7B are graphs depicting the frequency response and signal spatial linearity of the present invention.

FIG. 8A through FIG. 8E are graphs depicting test data from pig myocardium during control conditions, ischemia, and infusion of isoproterenol which compares the present invention with a conventional transit-time sonomicrometer.

DESCRIPTION OF THE PREFERRED EMBODIMENTS

Referring more specifically to the drawings, for illustrative purposes the present invention is embodied in the apparatus generally shown in FIG. 1 through FIG. 4. It will be appreciated that the apparatus may vary as to configuration and as to details of the parts, and that the method of the invention may vary as to the exact steps and their sequence, without departing from the basic concepts as disclosed herein. It will further be appreciated that, while exemplary circuitry is shown for the apparatus of the present invention, digital and analog equivalents of components and circuits can be used, and microcomputer implementations are also within the embodiments contemplated.

Figure 1:
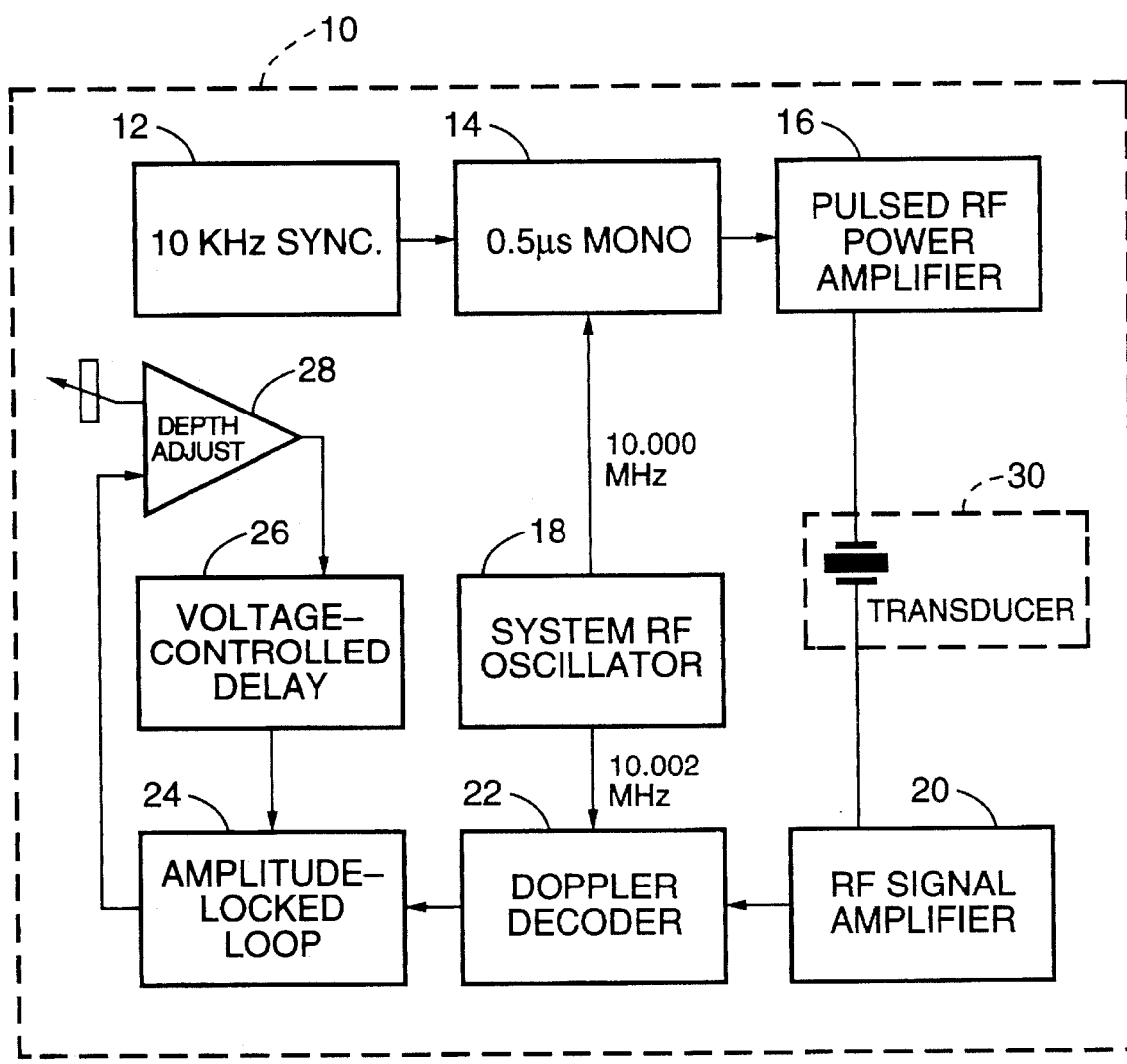
FIG. 1 is a functional block diagram of a single-crystal ultrasonic sonomicrometer in accordance with the present invention.

Referring to FIG. 1, a functional block diagram of a single-crystal ultrasonic sonomicrometer (SCS) 10 in accordance with the present invention is shown. As can be seen from FIG. 1, SCS 10 generally comprises a synchronization oscillator 12, a monostable 14, a pulsed RF power amplifier 16, a system RF oscillator 18, an RF signal amplifier 20, a Doppler decoder 22, an amplitude-locked-loop 24, a voltage-controlled delay 26, a depth adjustment 28, and a transducer 30. Synchronization oscillator 12, monostable 14, system RF amplifier 18, pulsed RF power amplifier 16 and transducer 30 make up the transmitting section, while transducer 30, RF signal amplifier 20, Doppler decoder 22, system RF amplifier 18, amplitude-locked-loop 24, voltage-controlled delay 26 and depth adjustment 28 make up the receiving section.

Figure 2A:
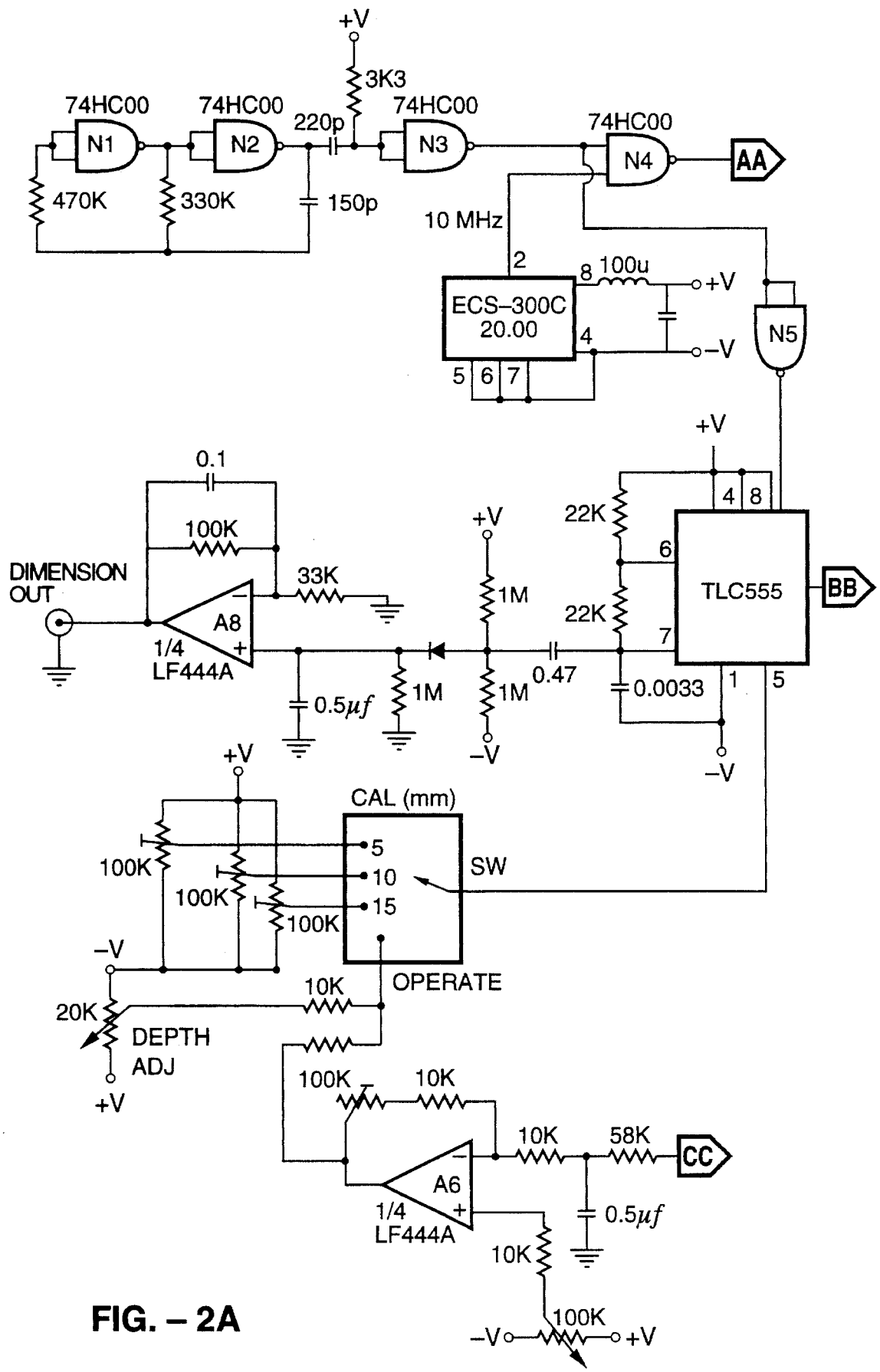
Figure 2C:
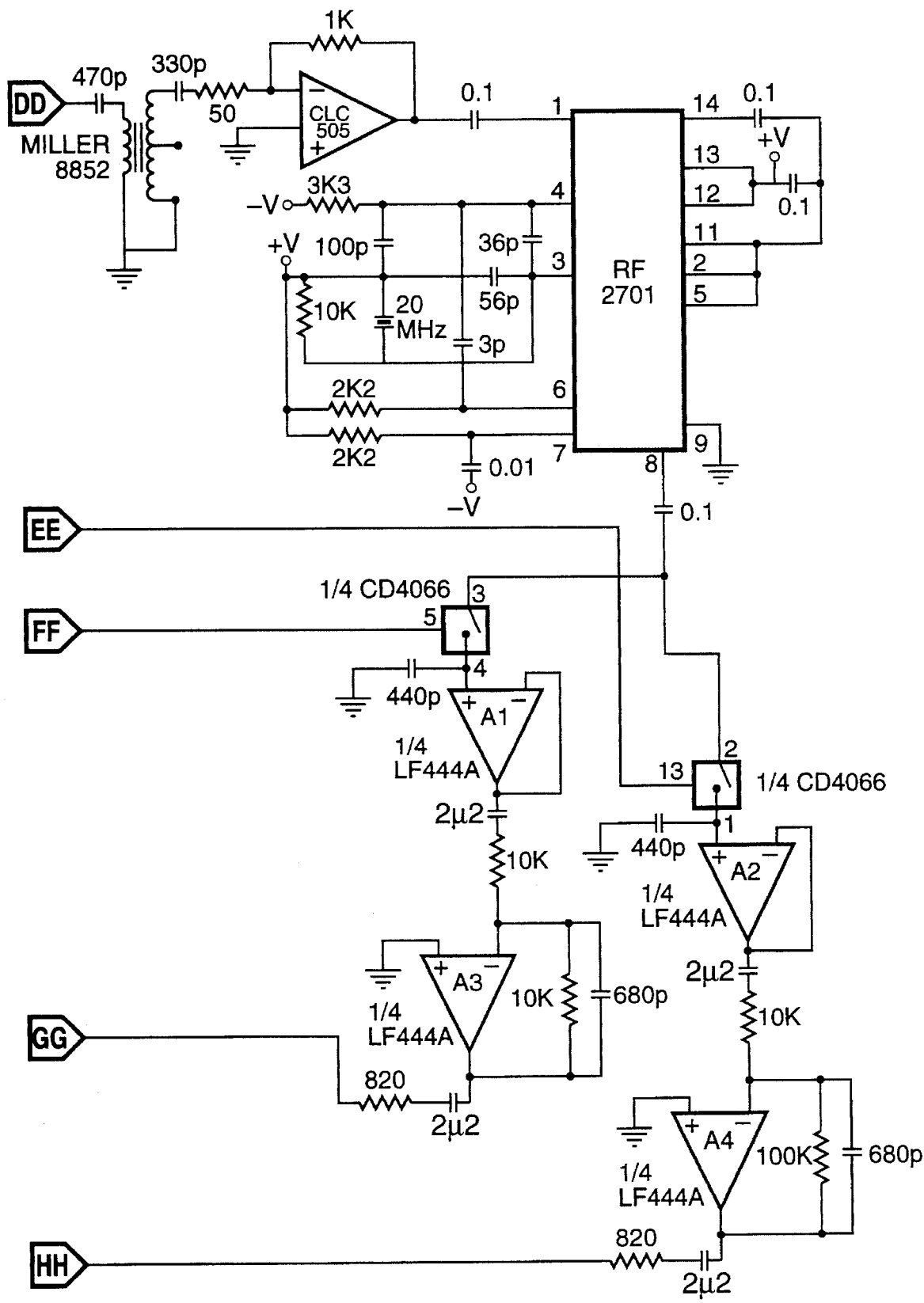

Referring also to FIG. 2, which shows a schematic diagram of an embodiment of circuitry implementing the configuration of the invention shown in FIG. 1, the present invention operates as follows. The synchronization oscillator 12, which is formed by two NAND gates (N1 and N2), oscillates at a 10 KHz frequency (SYNC). These NAND gates, as well as the other NAND gates used in the circuitry, are typically a 74HC00 or the like. On the falling edge of the SYNC signal, NAND gate N3, which is configured as a monostable 14, generates a 0.5 µs pulse that is applied to one of the inputs of NAND gate N4. The other input of NAND gate N4 is connected to the 10 MHz output of system RF oscillator 18 which is a crystal oscillator such as an ECS-300C 20.00 or the like. Therefore, every 100 ns, a 0.5 µs duration burst of 10 MHz pulses is generated. The resulting burst of pulses is applied in the input of pulsed RF power amplifier 16 which is of a high current type such as an EL7114 or the like. The output of pulsed RF power amplifier 16 is transformer-coupled to transducer 30 using a step-up RF transformer.

Myocardial layers and red blood cells in the ventricular chamber reflect the ultrasonic energy back to transducer 30. The reflected echoes are amplified by RF signal amplifier 20 which comprises a pair of CLC505 high frequency amplifiers or the like. The amplified signal is then applied to Doppler decoder 22, which is a quadrature decoder chip such as an RF2701 or the like, and mixed with system RF oscillator 18 at a 2 kHz offset relative to the frequency of the transmitted signal. When the offset signal is mixed with returning ultrasonic echoes, the resulting Doppler signals are shifted in the frequency domain by 2 kHz. The Doppler signal is then sampled at two separate time intervals using two sample-and-hold circuits formed by one-half of a CD4066 or the like and one-half of a LF444A or the like. The sample-and-hold circuits are triggered by a series of monostables formed by NAND gates N6, N7 and N8 which initiate their timing from the falling edge of the voltage-controlled delay 26 formed by a TLC555 or the like. The two Doppler signals are then bandpass filtered and amplified by the remaining one-half of the LF444A. Then, the two signals are applied into the amplitude-locked-loop (ALL) 24, which comprises two CA3080A AGC amplifiers or the like, two AD737 RMS-to-DC converters or the like and one-half of a LF444A or the like. This circuit compares the true RMS values of the two Doppler signals and generates an error signal when the steady-state condition changes. The wall thickness signal is the integrated error signal generated from ALL 24 throughout the cardiac cycle and can be calibrated electronically in vitro as well as in vivo. Integration of the error signal is performed using a conventional microcomputer or the like (not shown).

Figure 3:
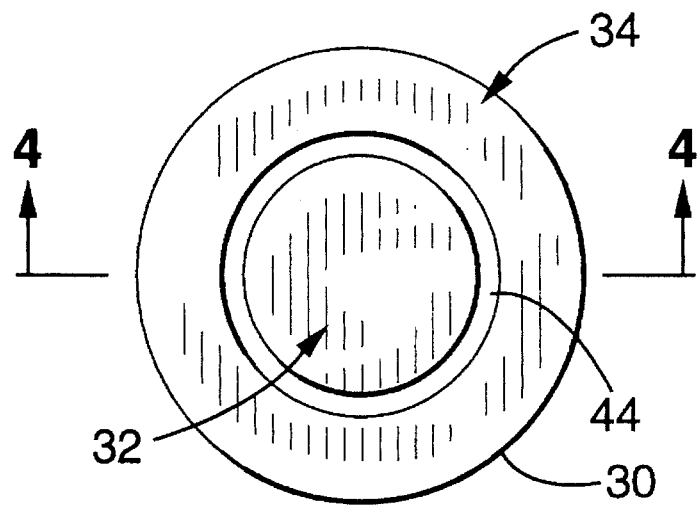
FIG. 3 is a plan view of the piezoelectric epicardial transducer portion of the present invention.
Figure 4:
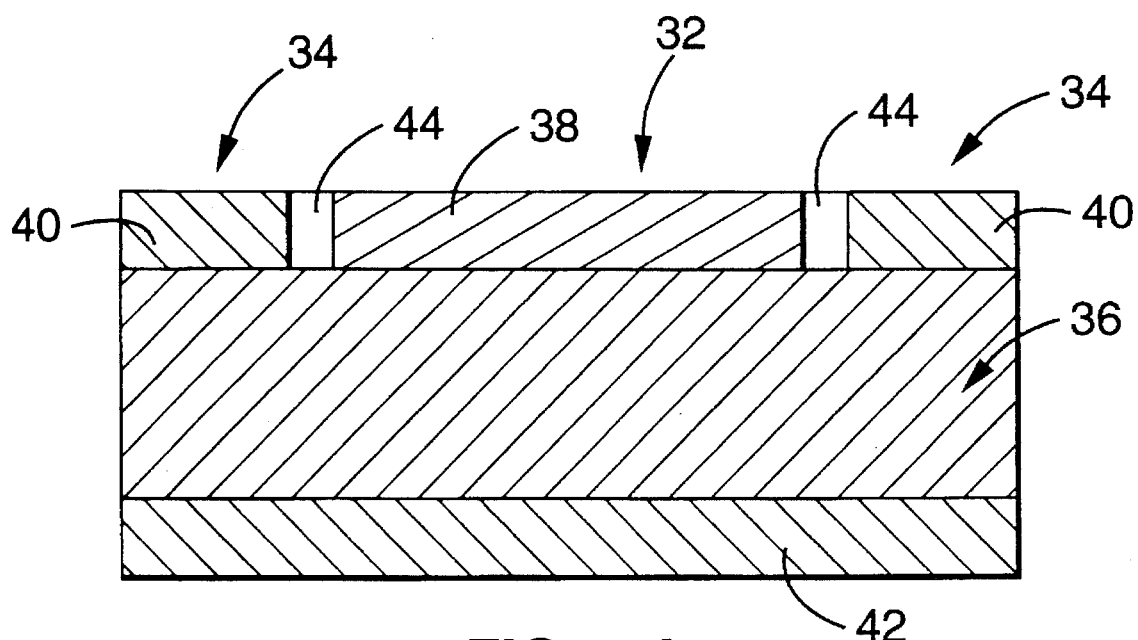
FIG. 4 is a cross-sectional view of the piezoelectric epicardial transducer shown in FIG. 3 taken through line 4—4.

Referring also to FIG. 3 and FIG. 4, transducer 30 is of an annular configuration and comprises separate transmitter 32 and receiver 34 areas located on the same piece of piezoelectric material 36 such as PZT5-A or the like. Transmitter area 32 is formed from a thin, disk-shaped metal electrode 38 and receiver area 34 is formed from a thin, annular metal electrode 40. Piezoelectric material 36 is sandwiched between the foregoing electrodes and a thin, metal bottom electrode 42. Preferably, transducer 30 should be as small as possible to enable a small ultrasonic beam width, while at the same time it should also be as large as possible to increase ultrasonic receiver sensitivity. Transducer 30 is typically fabricated by depositing a thin layer of metal on the top and bottom of piezoelectric material 36. The two concentric areas which make up transmitter electrode 38 and receiver electrode 40 are then formed by removing a small circular electrode band 44 of the deposited top metal layer with the aid of a dissecting microscope and scalpel. Bottom electrode 42, which is common both the transmitter and receiver areas, is formed by leaving the bottom metal layer intact. By employing this particular configuration, only the transmitter electrode 38 is energized during the transmitting phase, while during reception, both the transmitter electrode 38 and receiver electrode 40 are utilized. This results in optimized transmitted ultrasonic beam width pattern and directional sensitivity of the receiver. Typically, for a 4 mm diameter transducer, the diameter of the transmitter electrode 38 is 2.25 mm. For smaller than 2 mm diameter transducers, the transducers can be used without removing any top electrode area.

Figure 5:
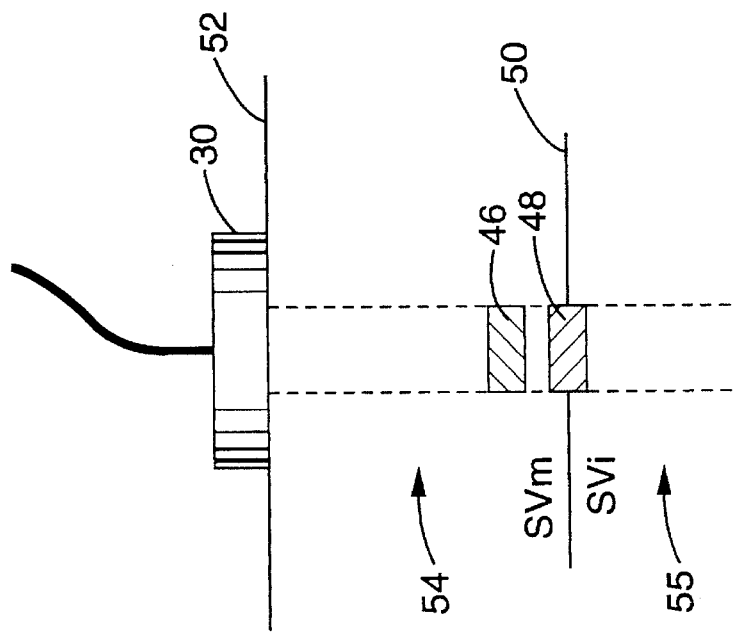
FIG. 5 is a diagrammatic view of a cross-section of myocardial tissue showing the position of sample volumes relative to the endocardium.

Referring also to FIG. 5, during calibration the Doppler decoded signal is initially sampled at two distinct time intervals corresponding to sample volumes $SV_m$ (reference) and $SV_i$ (interface). FIG. 5 diagrammatically depicts a cross-section of the myocardial wall to illustrate positioning of sample volumes $SV_m$ 46 and $SV_i$ 48 relative to the endocardium 50, as well as positioning of transducer 30 on the epicardium 52. For improved signal-to-noise ratio reception of ultrasonic Doppler echoes during steady-state, sample volume $SV_m$ 46 is adjusted so that it remains within the myocardium 54. After a small time delay, sample volume $SV_i$ 48 is positioned so that only half of the volume is in the myocardium 54, while the other half is situated in the ventricular chamber 55. Note that a significant aspect of the present invention is the positioning of the reference volume $SV_m$ 46 in the muscle, and the positioning of one-half of the interface volume $SV_i$ 48 in the muscle and one-half in the blood.

The outputs from these two sample volumes are bandpass filtered within the amplitude-locked loop circuit 24 to remove frequencies contributed by red blood cells. The true RMS values from both sample volumes then are compared and an error signal is generated. The integrated error signal is adjusted for correct depth placement using depth adjustment 28 and applied to the voltage-controlled delay 26. The amplitude-locked-loop 24 continuously adjusts the position of the two sample volumes $SV_m$ 46 and $SV_i$ 48, so that they always remain within, and thereby effectively track, the muscle/blood interface. This allows the SCS 10 to measure absolute myocardial wall thickness. The theoretical resolution of SCS 10 at a frequency of 10 MHz is approximately 20 µm, assuming a ten percent mismatch between the reference and interface echo processing circuits. Better resolution can be achieved by closer matching the circuit component tolerances of amplitude-locked loop 24 or by increasing the operating frequency of SCS 10. Note also that, in the preferred embodiment, transducer 30 is applied to the surface of the myocardium and depth adjustment 28 is adjusted until the returned echoes from the endocardium lock SCS 10 into tracking the endocardial blood/muscle interface. Also, while comparison of the RMS values of the signal levels from the sample volumes provides the greatest accuracy in measurements, other values could be compared.

EXAMPLE 1

The transducer 30 was sutured on the epicardium of a test subject over the area of interest. Transducer 30 had three small stainless-steel loops epoxied on the top surface allowing for quick placement and minimal damage to the epicardial surface of the myocardium. An oscilloscope was connected at the output of Doppler decoder 22 to view the Doppler echoes returning from the myocardium. The location of the sample volumes relative to the Doppler echoes also was shown on another oscilloscope channel. The oscilloscope was synchronized by the 10 kHz output of synchronization oscillator 12. The myocardial wall was easily identified by its large amplitude echoes versus the much smaller amplitude echoes from red blood cells within the ventricular chamber. Adjustment of depth adjustment 28 allowed placement of the sample volumes close to the moving myocardium and blood interface. Once the moving myocardial interface passed through the sample volumes, the single-crystal ultrasonic sonomicrometer of the present invention automatically began to track the interface. A rotary switch (FIG. 2A) provided three calibration steps (5, 10 and 15 mm).

EXAMPLE 2

In-vitro Evaluation

Figure 6:
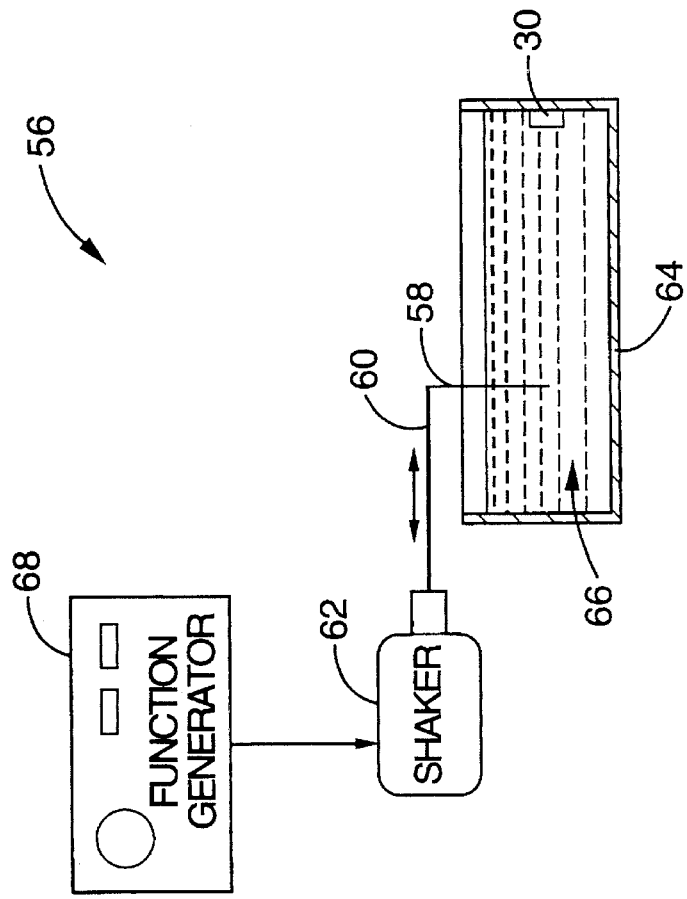
FIG. 6 is a diagrammatic view of an in-vitro test apparatus for evaluating accuracy, signal and spatial linearity, and frequency response of the present invention.

The test apparatus 56 shown in FIG. 6 was used to evaluate the accuracy, linearity and frequency response of SCS 10. A 3-cm long guide-wire 58 having a diameter of 0.08 mm was attached on the arm 60 of a shaker 62 (Ling Dynamics, model 411) and bent at a 90 degree angle to represent the endocardial layer. The maximum linear displacement of shaker 62 was 6 mm. Transducer 30 was placed in a container 64 of saline 66 into which guidewire 58 was inserted. Shaker 62 was driven by a function generator 68 adjusted to produce a frequency modulated triangular wave signal output with a frequency from DC to 20 Hz. SCS 10 was tested for spatial linearity at ranges of 5, 15 and 35 mm using a computer-based data acquisition and analysis system (EGAA, RC Electronics). Data obtained from the output of SCS 10 was compared with the output from the function generator 68. Accuracy was determined as the percent similarity between the output of SCS 10 and the output of the function generator 68. Linearity was evaluated by linear regression analysis, comparing the outputs of SCS 10 and the function generator 68. Frequency response was defined as the frequency limit when peak amplitude of the signal output was reduced by 5%.

The signals acquired to test accuracy, signal and spatial linearity, and frequency response of SCS 10 are shown in FIG. 7A and FIG. 7B as a function of time, where one division along the x-axis corresponds to one second. In FIG. 7A and 7B, the y-axis represents distance in millimeters, and in FIG. 7B the y-axis represents output voltage in volts. FIG. 7A shows that the upper and lower limits of motion for each of the test waveforms in segments A (5 mm), B (15 mm) and C (35 mm) were ±3 mm, the mechanical limits of shaker 62. FIG. 7B shows the output of the function generator 68 used to drive shaker 62. Results obtained from the this test shows that the invention accurately and linearly tracks an echo. For the three shaker arm positions of 5, 15 and 35 mm where measurements were taken, the accuracy was calculated as 99.2%, 99.3% and 99.3% respectively. Similarly, for the same three distances, the r-values for signal linearity were calculated as 0.994, 0.997 and 0.997, respectively. SCS 10 exhibited high fidelity frequency response from DC to >20 Hz during each of the distance measurements, the latter frequency corresponding to a heart rate >400 beats/min. Good spatial linearity was demonstrated by the good accuracy, signal linearity and sustained frequency response of the dimension measurement at each distance.

EXAMPLE 3

In-vivo Evaluation

To evaluate the capability of the present invention to accurately track the endocardial wall interface in-vivo, an experimental protocol was performed using anesthetized pigs. Adult domestic pigs of either sex were preanesthetized with ketamine (20 mg/kg, i.m.) and atropine (0.05 mg/kg, i.m.). After intubation, anesthesia was maintained by intravenous chloralose (100 mg/kg, i.v., initial bolus; 25 mg/kg every 30–60 min intervals).

A 10 MHz transit-time receiver circuit was used in conjunction with the present invention to provide comparison between the two systems. To facilitate this comparison, a special in-vivo test transducer was designed and built. This transducer was constructed by adding a 1 mm wide outer transmitting ring to transducer 30, thereby enabling the transducer to act both as a transmitter-receiver for SCS 10 and as a transmitter for the conventional two-crystal transit-time sonomicrometer (TTS). This design permitted the receiver transducer of the conventional TTS to receive the ultrasonic energy from the transducer of SCS 10 without being directly underneath, which would cause an artificially large echo. The outside diameter of the in-vivo test transducer was approximately 5 mm. This transducer was secured to the surface of the epicardium of the left ventricle. Subsequently, a 10 MHz, 1.5 mm diameter TTS transducer with a convex epoxy lens was inserted at an angle to a position adjacent to the endocardial surface. Care was taken not to insert the endocardial transducer under the transmitting area of the epicardial transducer by monitoring both SCS 10 and the conventional TTS RF output signals on an oscilloscope. Position of the endocardial crystal was confirmed postmortem.

Figure 8A:
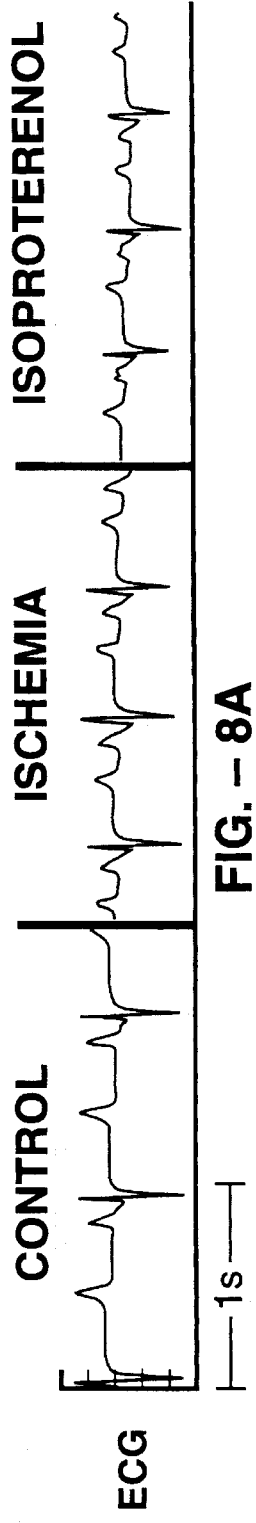
Figure 8B:
Figure 8C:
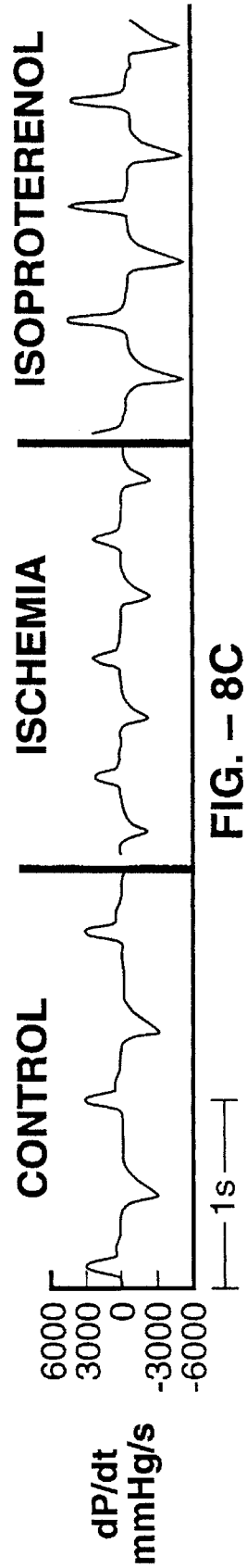

The in-vivo protocol consisted of measurements during control conditions, reduced myocardial function (ischemia caused by complete occlusion of the proximal coronary artery), and increased myocardial function (isoproterenol, 2 μg bolus, iv). The data in FIG. 8A through FIG. 8E illustrates three segments of raw data during control, ischemia and infusion of isoproterenol conditions in relation to time in seconds. FIG. 8A shows the electrocardiogram (ECG) waveforms, FIG. 8B shows the left ventricular pressure (LLV) in millimeters of mercury, FIG. 8C shows the change in left ventricular pressure per time (dP/dt) in millimeters of mercury per second, FIG. 8D shows the corresponding myocardial wall motion measured by SCS 10 in millimeters, and FIG. 8E shows the corresponding myocardial wall motion measured by the conventional TTS. As can be seen, the output waveforms of the SCS 10 and the conventional TTS were nearly identical with each other throughout the three interventions.

Measurements of end-systolic, end-diastolic and percent wall thickness from both the conventional TTS and SCS 10 were derived on-line using a computer-based data acquisition and analysis system (EGAA, RC Electronics). The left ventricular dP/dt signal was used by the acquisition and analysis system to extract timing points for end-systole and end-diastole. The timing algorithm selected end-diastolic dimensions (EDD) from the onset of the upstroke of positive dP/dt waveform, while end-systolic dimensions (ESD) were selected at a time 20 ms before peak negative dP/dt. Percent wall thickness was calculated as % WTh=100[(ESD−EDD)/EDD].

Figure 9:
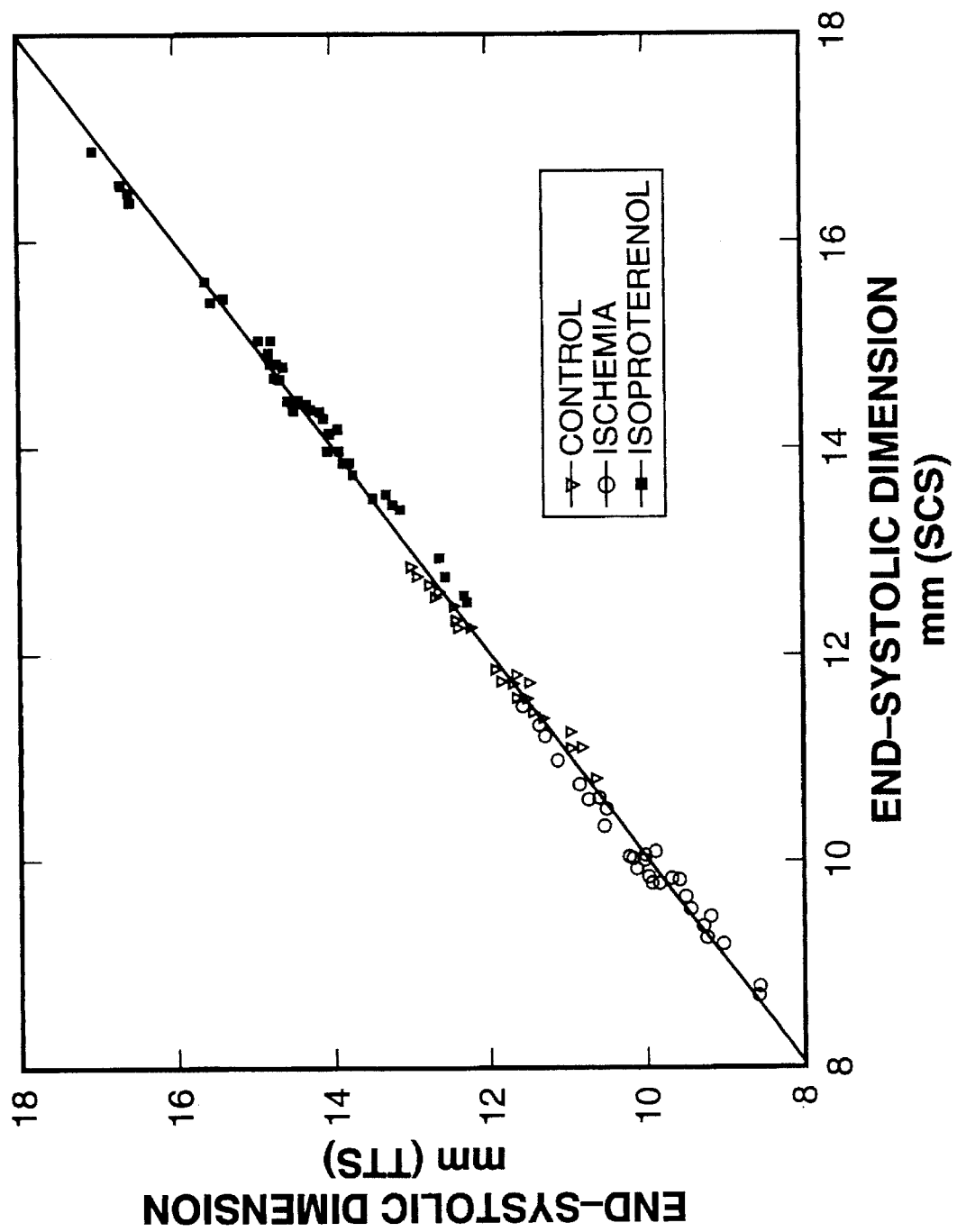
FIG. 9 is a graph comparing the linearity of the present invention with that of a conventional transit-time sonomicrometer for end-systolic dimensions during control conditions, ischemia and infusion of isoproterenol.
Figure 10:
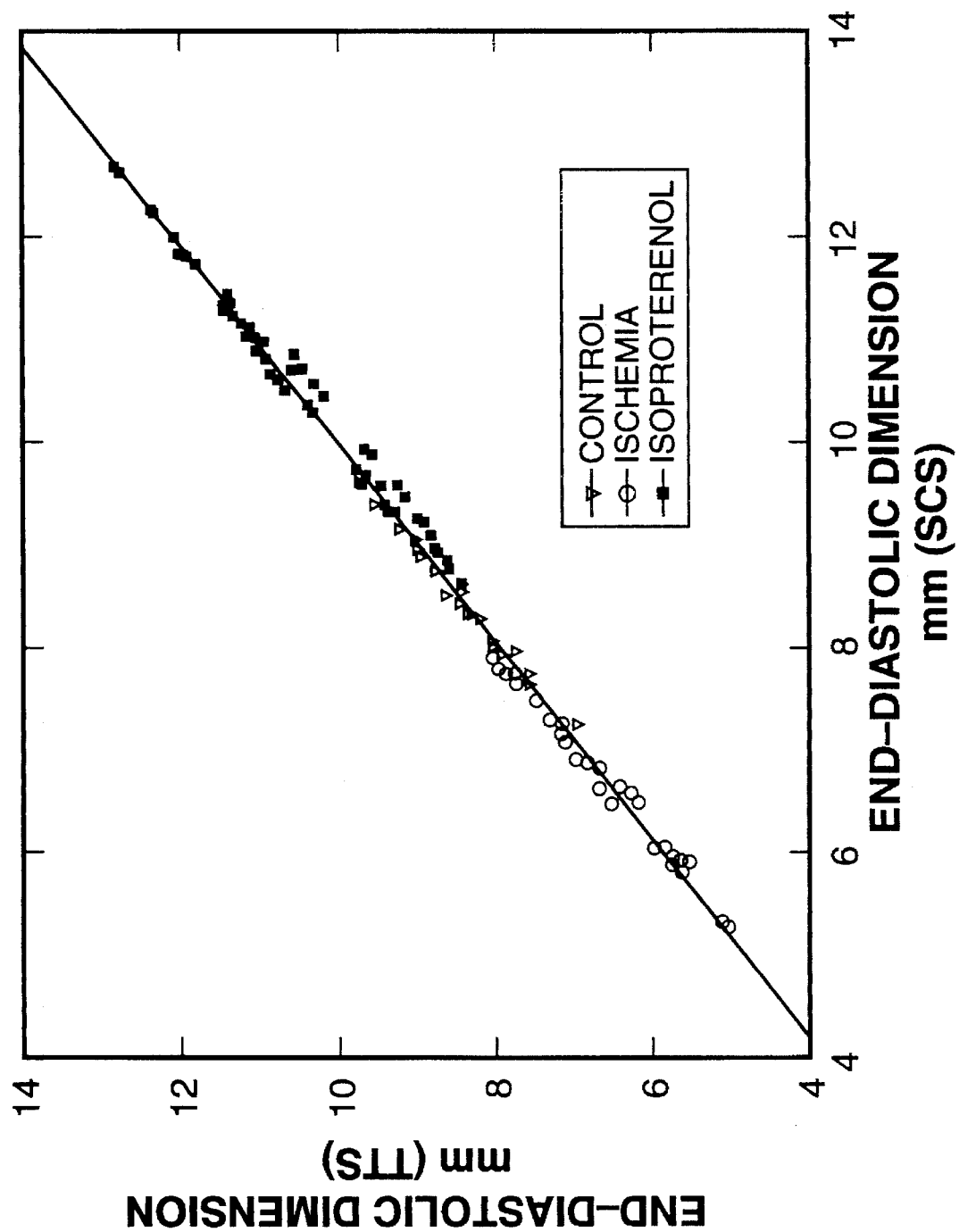
FIG. 10 is a graph comparing the linearity of the present invention with that of a conventional transit-time sonomicrometer for end-diastolic dimensions during control conditions, ischemia and infusion of isoproterenol.
Figure 11:
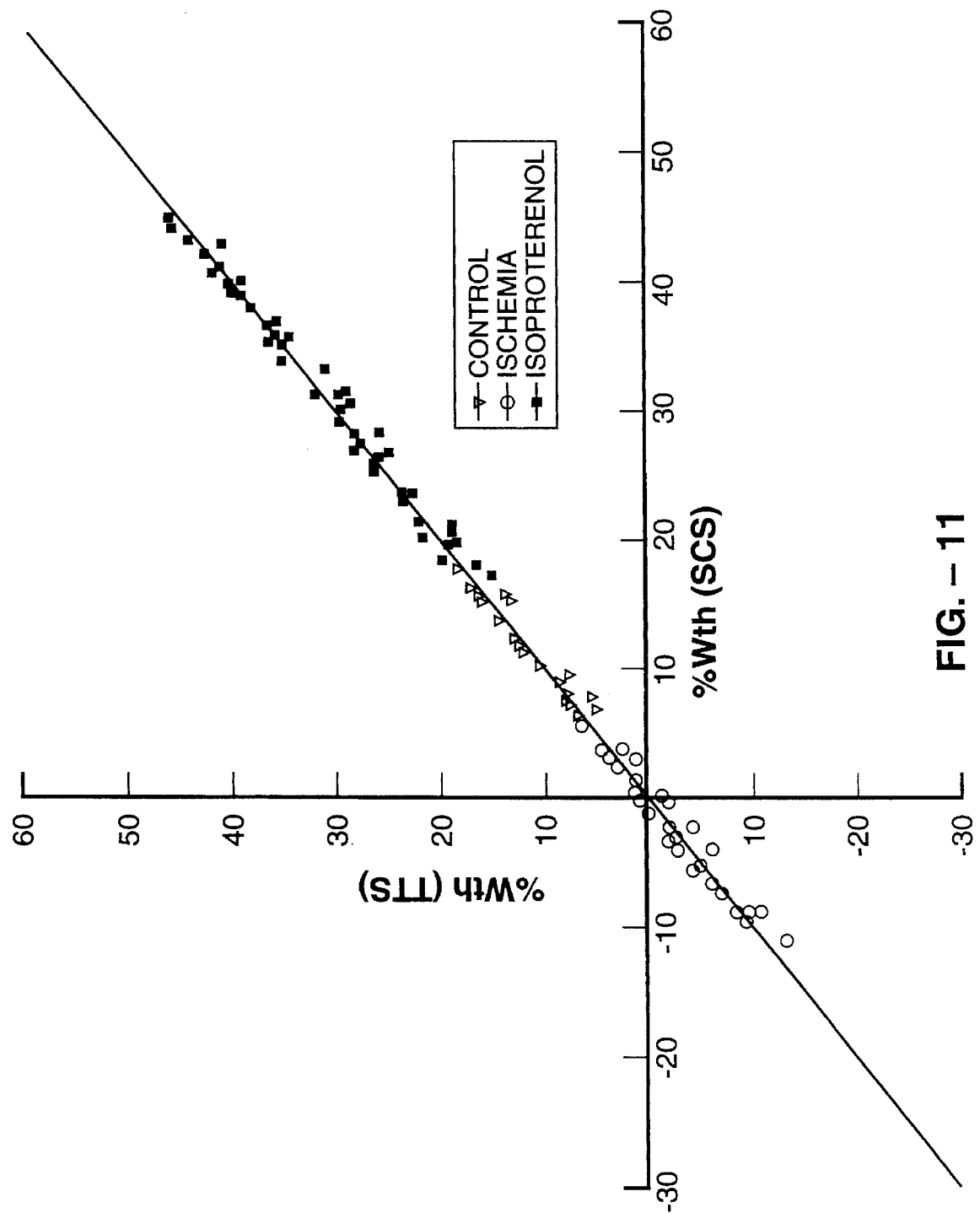
FIG. 11 is a graph comparing calculated wall thickness using the present invention with that using a conventional transit-time sonomicrometer for end-diastolic dimensions during control conditions, ischemia and infusion of isoproterenol.

Referring to FIG. 9 through FIG. 11, a summary of the results for three animals which were each instrumented with both an epicardial and an endocardial transducer is shown. FIG. 9 shows data for end-systolic dimensions, FIG. 10 shows data for end-diastolic dimensions, and FIG. 11 shows the calculated percent wall thickness during control conditions, ischemia (coronary occlusion) and infusion of isoproterenol. Data were collected at the times of transition between the three interventions to compare SCS 10 and the conventional TTS signals over a wide range of measured end-systolic and end-diastolic thicknesses as well as calculated percent wall thickness. A total of 122 paired measurements for each parameter were acquired and analyzed using the computer-based data acquisition and analysis system. End-systolic measurements ranged from 8.6 to 17.2 mm and displayed a linear regression equation of y=−0.128+1.008x. End-diastolic measurements ranged between 5.2 and 12.9 mm, yielding a linear regression equation of y=−0.300+1.031x. Calculated values for percent wall thickness ranged from −10.7 (i.e., thinning) to +48.6% yielding a linear regression equation of y=−0.076+1.000x. The linear correlation coefficients (r values) for all three equations were 0.99. For all three linear regression equations, the y intercepts were offset from zero by an insignificant amount; none of the slopes were significantly different from unity.

As can be seen from the foregoing, SCS 10 uses a closed-loop paradigm to track the endocardial muscle/blood interface and measure absolute myocardial dimensions. Its design is more closely related to clinical M-mode echocardiographic methods and the conventional TTS rather than currently available Doppler displacement systems. However, measurement of myocardial dimensions using clinical echocardiographic methods is prohibitively expensive for most research laboratories, and the use of the conventional TTS requires the insertion of an endocardial transducer.

SCS 10 exhibits good accuracy, signal and spatial linearity and frequency response as shown by the data in FIG. 7A and FIG. 7B. We have also demonstrated that SCS 10 accurately tracked a wire induced echo up to a maximum displacement of 6 mm, a limitation imposed by the available shaker. The maximum displacement that SCS 10 can track depends upon the gain of the feedback loop that adjusts the position of the two sample volumes. We found that there is a trade-off between maximum displacement and baseline stability when motion of the muscle/blood interface was stationary or very low (e.g during acute ischemia). For the 10 MHz apparatus described herein, the gain of the feedback loop was adjusted so that maximum displacement was limited to approximately 25 mm while the transducer was moved manually in the saline container. This ensured baseline stability even when the input signal was stationary as can be seen in FIG. 7A and FIG. 7B. The 25 mm displacement is adequate for the range of heart sizes for which this system was designed (e.g, mini-pigs, dogs and large farm pigs). For these hearts, a displacement of 25 mm would be >100% of the wall thickness. The output waveforms of SCS 10 shown in FIG. 7 also demonstrate the high degree of responsiveness of the closed-loop circuit to abrupt changes in both amplitude and direction of the driving triangular waveform. As a result, the output waveforms of SCS 10 and the function generator 68 shown in FIG. 7A and FIG. 7B are virtually indistinguishable. Also of interest is the response of the system to the stationary portion of the test waveforms. Even though the actual Doppler frequency received from that position was probably zero, the sample volumes $SV_m$ and $SV_i$ remain locked onto the guide-wire position due to the 2 kHz offset signal mixed with the returned echoes. This offset signal also is necessary during in-vivo situations when the myocardial muscle attains very low velocities, e.g., during diastole in bradycardic and extended ischemic interventions. These low velocities generate very low frequency Doppler signals approximately in the order of 1 to 30 Hz, which are within the frequency response of SCS 10, and would create unacceptable compromises between response time and accuracy of the tracked signal. This trade-off was avoided when the Doppler signal was shifted, since the lowest Doppler frequency was now much higher than the maximum myocardial frequency response.

A number of in-vivo evaluations of SCS 10 were also performed to evaluate its usefulness in measuring physiological variables such as end-systolic and end-diastolic dimensions and percent wall thickness. The evaluation protocol was designed to induce two extreme conditions including myocardial dysfunction and hyperfunction. The invention proved to be an effective method to accurately measure end-systolic and end-diastolic dimensions as well as percent wall thickness, when these parameters were compared with a conventional two-crystal TTS as shown in FIG. 8A through FIG. 8E. We observed no systematic over- or underestimation by SCS 10 measuring end-systolic and -diastolic dimensions and percent wall thickness compared with the conventional TTS; the data points were found to be very close to the line of identity for the two systems as can be seen in FIG. 9 through FIG. 11.

Although we have not evaluated or compared SCS 10 with conventional Doppler displacement systems, some known parameters can be compared. For instance, conventional Doppler displacement systems provide only a relative measurement of displacement, while SCS 10 can track the actual position of the endocardial blood interface, thus, it can measure absolute myocardial dimensions. Furthermore, conventional Doppler displacement systems require a reset mechanism synchronized with the R-wave of the ECG signal to prevent the accumulation of various error voltages on the output signal. The reset mechanism causes the output signal to reset to a preset value, requiring the user to adjust the sample volume position and recalibrate every time there is a marked change in end-diastolic dimension. SCS 10, however, does not require a reset mechanism; it is calibrated only once at the beginning of the experiment. Therefore, two major limitations of the Doppler displacement systems have been eliminated by the present invention.

It can be noted that the single piezoelectric transducer used in conjunction with the present invention was designed to address the special receiving and transmitting ultrasonic wave profiles required for this system. The transmitting ultrasonic wave profile needed to have a small near field illumination to achieve good lateral resolution, while the receiving ultrasonic wave profile needed to be wide, to increase directional sensitivity of the ultrasonic receiver. Disk-shaped transducers usually compromise one of the two profiles, while using two physically separate transducers creates a problem of beam alignment and adds to the complexity of manufacturing the transducer. We designed the single transducer used in the present invention to optimize both the transmitting and receiving ultrasonic wave profiles without compromising the function of either one.

Note also that the spatial resolution of the present invention is approximately 1 mm, which means that this apparatus can identify two objects as being distinct, only if they are separated by more than 1 mm. Therefore, for proper identification of the myocardial muscle/blood interface by the sampling volumes $SV_m$ and $SV_i$, the area underneath this interface must be free for at least 1 mm from any structures such as the septum, papillary muscles and/or trabeculae, that may generate an echo. If a structure such as a papillary muscle is present and generates an echo situated less than 1 mm apart from the muscle/blood interface, the invention locks on the papillary muscle echo and the measurement of end-systolic and end-diastolic dimensions is overestimated. Throughout our tests and evaluations of this system in pigs, we have not experienced this problem, because the papillary muscles are separating >1 mm from the endocardium at the region closer to the base of the heart. In general, usable area of the heart for our system is large enough to function properly.

Accordingly, it can be seen that we have developed and evaluated an ultrasonic instrument that uses a single epicardial transducer to measure absolute myocardial dimensions. When the single-crystal ultrasonic sonomicrometer of the present invention was compared with a conventional two-crystal transit-time sonomicrometer it was shown to have >99% signal accuracy, signal linearity correlation coefficient of 0.99, frequency response from DC to at least 20 Hz and good spatial linearity. These characteristics make the present invention useful throughout a broad range of end-systolic and end-diastolic dimensions and percent wall thicknesses.

Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An apparatus for measuring the thickness of the myocardial wall in a heart, comprising:
   (a) transmitting means for transmitting an ultrasonic signal;
   (b) receiving means for receiving an ultrasonic signal which is a reflection of said transmitted ultrasonic signal;
   (c) transducer means electrically coupled to said transmitting means and said receiving means for emitting and detecting said transmitted and received ultrasonic signals; and
   (d) means associated with said transmitting and receiving means for acquiring a reflected signal from a first volumetric region within the myocardium of the heart so as to spatially position a reference volume within the myocardium, for acquiring a reflected signal from a second volumetric region wherein one-half of said second volumetric region is within said myocardium and one-half of said second volumetric region is within the adjacent ventricular chamber so as to spatially position an interface volume at the endocardial muscle/blood interface, for comparing signal levels from said reference volume and said interface volume at successive time intervals during a cardiac cycle, and for generating an output signal indicative of a differential in said signal levels.

2. An apparatus as recited in claim 1, further comprising:
   (a) sampling means for sampling said received signal at successive time intervals; and
   (b) means for adjusting the positions of said reference volume and said interface volume to track the endocardial muscle/blood interface.

3. A method of measuring myocardial wall thickness using an apparatus as recited in claim 2, comprising the steps of:
   (a) subjecting said heart to a transmitted signal comprising ultrasonic pulses generated by said transmitting means and directed toward said heart by said transducer means;
   (b) receiving, with said transducer means and said receiving means, a received signal which is a reflection of said transmitted signal from said heart;
   (c) positioning said reference volume within the myocardium of said heart;
   (d) positioning one-half of said interface volume within said myocardium and one-half of said interface volume within the adjacent ventricular chamber;
   (e) sampling said received signal at successive time intervals;
   (f) comparing signal levels at said successive time intervals during a cardiac cycle; and
   (g) generating an output signal indicative of a differential in said signal levels.

4. A method as recited in claim 3, further comprising the step of adjusting the positions of said reference volume and said interface volume to track the endocardial muscle/blood interface of said heart.

5. A method as recited in claim 4, further comprising the step of integrating the differential in signal levels throughout the cardiac cycle to determine myocardial wall thickness.

6. An apparatus as recited in claim 1, wherein said transducer means comprises:
   (a) a generally cylindrical piezoelectric substrate, said substrate having first and second generally planar surfaces, said substrate having a central axis extending between said first and second surfaces;
   (b) a transmitting electrode deposited on said first surface of said substrate, said transmitting electrode having first and second generally planar surfaces, said second surface of said transmitting electrode positioned adjacent to said first surface of said substrate;
   (c) a receiving electrode deposited on said first surface of said substrate, said receiving electrode having first and second generally planar surfaces, said second surface of said receiving electrode positioned adjacent to said first surface of said substrate;
   (d) said transmitting and receiving electrodes being coaxially aligned with said central axis and separated by an annular groove extending from said first surfaces of said electrodes to said first surface of said substrate, said annular groove being coaxially aligned with said central axis; and
   (e) a common electrode deposited on said second surface of said substrate.

7. An apparatus as recited in claim 1, wherein said transducer means comprises:
   (a) a piezoelectric substrate layer having first and second surfaces;
   (b) first and second concentric electrode layers adjacent to said first surface of said substrate; and
   (c) a third electrode layer adjacent to said second surface of said substrate;
   (d) wherein said first and second concentric electrode layers are spaced apart from said third electrode layer, and wherein said first and second electrode layers are separated by an annular groove extending between said first and second electrode layers and said first surface of said substrate.

8. A single-crystal sonomicrometer apparatus for measuring myocardial wall thickness in a heart, comprising:

(a) transmitting means for transmitting an ultrasonic signal;

(b) receiving means for receiving an ultrasonic signal which is a reflection of said transmitted ultrasonic signal;

(c) a generally cylindrical piezoelectric substrate, said substrate having first and second generally planar surfaces, said substrate having a central axis extending between said first and second surfaces;

(d) a transmitting electrode deposited on said first surface of said substrate, said transmitting electrode having first and second generally planar surfaces, said second surface of said transmitting electrode positioned adjacent to said first surface of said substrate;

(e) a receiving electrode deposited on said first surface of said substrate, said receiving electrode having first and second generally planar surfaces, said second surface of said receiving electrode positioned adjacent to said first surface of said substrate;

(f) said transmitting and receiving electrodes being coaxially aligned with said central axis and separated by an annular groove extending from said first surfaces of said electrodes to said first surface of said substrate, said annular groove being coaxially aligned with said central axis;

(g) a common electrode deposited on said second surface of said substrate;

(h) said transmitting electrode electrically coupled to said transmitting means, said receiving electrode electrically coupled to said receiving means, said common electrode electrically coupled to said transmitting means and said receiving means;

(i) means for acquiring a reflected signal from a first volumetric region within the myocardium of the heart so as to spatially position a reference volume within the myocardium;

(j) means for acquiring a reflected signal from a second volumetric region wherein one-half of said second volumetric region is within said myocardium and one-half of said second volumetric region is within the adjacent ventricular chamber so as to spatially position an interface volume at the endocardial muscle/blood interface;

(k) means for sampling signal levels from said reference volume and said interface volume at successive time intervals during a cardiac cycle; and (l) means for comparing sampled signal levels from said reference volume and said interface volume at successive time intervals.

9. A method of measuring myocardial wall thickness using the apparatus recited in claim 8, comprising the steps of:

(a) subjecting said heart to a transmitted signal comprising ultrasonic pulses generated by said transmitting means (b) receiving an ultrasonic signal which is a reflection of said transmitted signal from said heart;

(c) positioning said reference volume within the myocardium of said heart;

(d) positioning one-half of said interface volume within said myocardium and one-half of said interface volume within the adjacent ventricular chamber;

(e) sampling said received signal at successive time intervals;

(f) comparing signal levels at said successive time intervals during a cardiac cycle; and (g) generating an output signal indicative of a differential in said signal levels.

10. A method as recited in claim 9, further comprising the step of adjusting the positions of said reference volume and said interface volume to track the endocardial muscle/blood interface of said heart.

11. A method as recited in claim 10, further comprising the step of integrating the differential in signal levels throughout the cardiac cycle to determine myocardial wall thickness.

12. A sonomicrometer apparatus for measuring myocardial wall thickness in a heart, comprising:

(a) transmitting means for transmitting an ultrasonic signal;

(b) receiving means for receiving an ultrasonic signal which is a reflection of said transmitted ultrasonic signal;

(c) a piezoelectric substrate layer having first and second surfaces;

(d) first and second concentric electrode layers adjacent to said first surface of said substrate; and (e) a third electrode layer adjacent to said second surface of said substrate;

(f) wherein said first and second concentric electrode layers are spaced apart from said third electrode layer, and wherein said first and second electrode layers are separated by an annular groove extending between said first and second electrode layers and said first surface of said substrate;

(g) said first electrode layer electrically coupled to said transmitting means, said second electrode layer electrically coupled to said receiving means, said third electrode layer electrically coupled to said transmitting means and said receiving means;

(h) means for acquiring a reflected signal from a first volumetric region within the myocardium of the heart so as to spatially position a reference volume within said myocardium;

(i) means for acquiring a reflected signal from a second volumetric region wherein one-half of said second volumetric region is within said myocardium and one-half of said second volumetric region is within the adjacent ventricular chamber so as to spatially position an interface volume at the endocardial muscle/blood interface;

(j) means for sampling signal levels from said reference volume and said interface volume at successive time intervals during a cardiac cycle; and (k) means for comparing sampled signal levels from said reference volume and said interface volume at successive time intervals.

13. A method for measuring the thickness of the myocardial wall in a heart, comprising the steps of:

(a) subjecting the heart to a transmitted signal comprising ultrasonic pulses;

(b) receiving an ultrasonic signal which is a reflection of said transmitted signal from the heart;

(c) acquiring a reflected signal from a first volumetric region within the myocardium of the heart so as to spatially position a reference volume within the myocardium;

(d) acquiring a reflected signal from a second volumetric region wherein one-half of said second volumetric region is within said myocardium and one-half of said second volumetric region is within the adjacent ventricular chamber so as to spatially position an interface volume at the endocardial muscle/blood interface;

(e) comparing signal levels from said reference volume and said interface volume at successive time intervals during a cardiac cycle; and (f) generating an output signal indicative of a differential in said signal levels.

14. A method as recited in claim 13, further comprising the steps of adjusting the positions of said reference volume and said interface volume to track the endocardial muscle/blood interface of said heart.

15. A method as recited in claim 13, further comprising the steps of integrating the differential in signal levels throughout the cardiac cycle to determine myocardial wall thickness.

16. A method for measuring absolute myocardial wall thickness in a heart, comprising the steps of:

(a) subjecting the heart to a transmitted signal comprising ultrasonic pulses;

(b) receiving an ultrasonic signal which is a reflection of said transmitted signal from the heart;

(c) acquiring a reflected signal from a first volumetric region within the myocardium of the heart so as to spatially position a reference volume within the myocardium;

(d) acquiring a reflected signal from a second volumetric region wherein one-half of said second volumetric region is within said myocardium and one-half of said second volumetric region is within the adjacent ventricular chamber so as to position an interface volume at the endocardial muscle/blood interface of the heart;

(e) adjusting the positions of said reference volume and said interface volume to track the endocardial muscle/blood interface of said heart;

(f) comparing the RMS signal levels from said reference volume and said interface volume at successive time intervals during a cardiac cycle;

(g) generating an output signal indicative of a differential in said signal levels; and (h) integrating the differential in signal levels throughout the cardiac cycle to determine myocardial wall thickness.

* * * * *